US007498318B1

(12) United States Patent
Stahl et al.

(10) Patent No.: US 7,498,318 B1
(45) Date of Patent: Mar. 3, 2009

(54) FOOD FOR DIABETICS

(75) Inventors: Bernd Stahl, Friedrichsdorf (DE); Michael Kliem, Aurachtal-Falkendorf (DE); Sandra Farwer, Erlangen (DE); Gunther Sawatzki, Munzenberg (DE); Gunther Boehm, Echzell (DE)

(73) Assignee: N.V. Nutricia, HM Zoetermeer (NL)

( * ) Notice: Subject to any disclaimer, the term of this patent is extended or adjusted under 35 U.S.C. 154(b) by 0 days.

(21) Appl. No.: 10/129,095

(22) PCT Filed: Nov. 10, 2000

(86) PCT No.: PCT/EP00/11134

§ 371 (c)(1),
(2), (4) Date: Aug. 15, 2002

(87) PCT Pub. No.: WO01/33973

PCT Pub. Date: May 17, 2001

(30) Foreign Application Priority Data

Nov. 11, 1999 (DE) ................................ 199 54 233

(51) Int. Cl.
*A61K 31/718* (2006.01)
(52) U.S. Cl. ...................................................... 514/58
(58) Field of Classification Search ................... 514/54, 514/57–61
See application file for complete search history.

(56) References Cited

U.S. PATENT DOCUMENTS

| 4,219,571 | A | | 8/1980 | Miyake | |
| 5,378,831 | A | * | 1/1995 | Usui et al. | 536/123.1 |
| 5,470,839 | A | * | 11/1995 | Laughlin et al. | 514/53 |
| 5,505,981 | A | * | 4/1996 | Wakabayashi et al. | 426/658 |
| 5,827,526 | A | * | 10/1998 | Dohnalek et al. | 424/440 |
| 6,596,696 | B1 | * | 7/2003 | Uchida et al. | 514/27 |

FOREIGN PATENT DOCUMENTS

| DE | 197 01 382 A1 | | 7/1998 |
| DE | 198 36 339 A1 | | 2/2000 |
| EP | 0 756 828 A1 | | 2/1997 |
| EP | 0 768 043 A2 | | 4/1997 |
| JP | 4-279596 | * | 5/1992 |
| WO | WO 96/31129 A1 | | 9/1996 |
| WO | WO 00 08948 A | | 2/2000 |

OTHER PUBLICATIONS

JPO abstract of JP 4-279596.*
Chronakis, I. "On the molecular characteristics, compositional properties, and structural-functional mechanisms of maltodextrins: a review" Crit. Rev. Food Sci. (1998) vol. 38, No. 7, pp. 599-637.*
Tsuji, K. et al "Energy value of a mixed glycosidic linked dextrin determined in rats" J. Agric. Food Chem. (1998) vol. 46, No. 6, pp. 2253-2259.*
Marchal, L. et al "Towards a rational design of commerical maltodextrins" Trends Food Sci. (1999) vol. 10, pp. 345-355.*
Fu D. et al., "Maltodextrin Accepter Reactions of *Streptococcus-mutans* 6715 Glucosyltransferases", Carbohydrate Research, Bd. 217, 1991, Seiten 201-212, XP002166087.
Fu D. et al., "Acceptor Reactions of Maltodextrins with *Leuconostoc-mesenteroides* B-512FM Dextransucrase", Archives of Biochemistry and Biophysics, Bd. 283, Nr. 2, 1990, Seiten 379-387, XP000992861.
Qu-Ming Gu: "Enzyme-mediated reactions of oligosaccharides and polysaccharides", J. Environ Polym Degrad; Journal of Environmental Polymer Degradation 1999, Kluwer Academic/Plenum Publ. Corps., NewYork, NY, Bd. 7, Nr. 1, 1999, Seiten 1-7, XP000992950.
Rendleman J. A. Jr.: "Enhanced production of Nd-cyclodextrin from corn syrup solids by means of cyclododecanone as selective complexant.", Carbohydrate Research 1993 Biopolymer Res. Unit, Nat. Cent. For Agric. Util. Res., USDA, ARS, Peoria, IL 61604, Bd. 247, Seiten 223-237, XP000394390.

* cited by examiner

*Primary Examiner*—Leigh C Maier
(74) *Attorney, Agent, or Firm*—Bacon & Thomas, PLLC

(57) ABSTRACT

Provided is a carbohydrate mixture comprising at least one modified carbohydrate from a base body and a carbohydrate residue coupled therewith. The base body concerned is either a digestible glucose-containing carbohydrate in the form of a digestible glucan or a non-digestible reserve carbohydrate, skeletal carbohydrate or a low-molecular component thereof. By coupling the base body with a carbohydrate residue, the glucose release from the inventive carbohydrate mixture is reduced by at least 10%, determined in an in-vivo digestion system on the basis of pancreatine and compared with a carbohydrate mixture containing the same amount by weight of non-modified carbohydrates. By means of the inventive carbohydrate mixture, the postprandial blood glucose concentration after eating can be moderated. The glucose can thus be metabolized by diabetics in spite of the existing lack of insulin. The inventive carbohydrate mixtures can be used in food for diabetics and in pharmaceuticals.

6 Claims, 1 Drawing Sheet

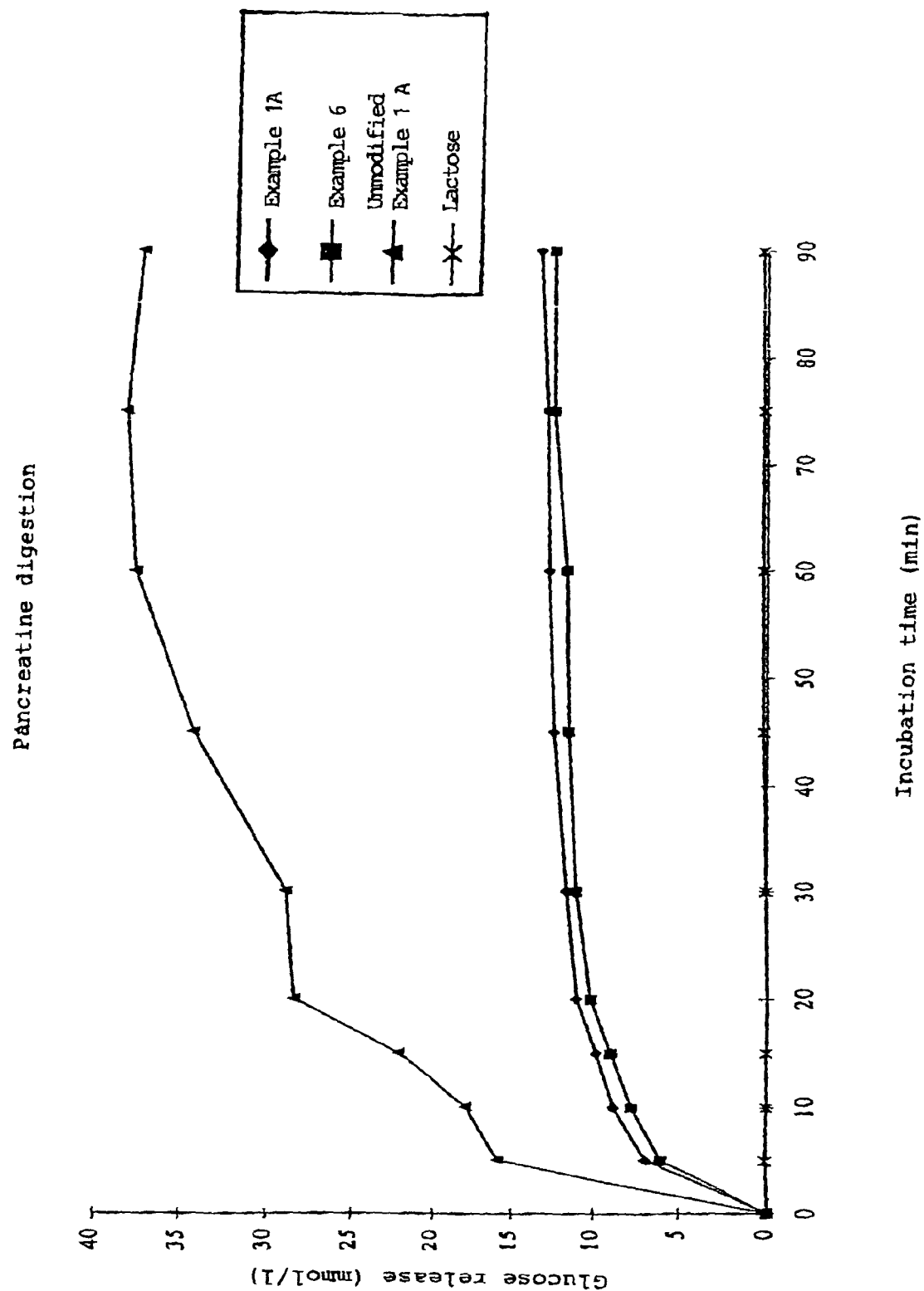

FOOD FOR DIABETICS

The invention relates to a carbohydrate mixture on the basis of conventional carbohydrates used for nutrition purposes for administration to diabetics or for the preparation of food or pharmaceuticals for diabetics, a preparation containing said carbohydrate mixture in the form of a food or pharmaceutical for diabetics, and the use of said carbohydrate mixture for administration to diabetics or for the preparation of food for diabetics or pharmaceuticals.

Feeding of glucose-containing carbohydrates is critical for diabetics, since due to the lack of insulin, the glucose present in the body after the digestion of these foodstuffs, and the subsequent intake of the glucose into the bloodstream cannot be utilized in a quantitatively sufficient manner. The consequence thereof is a high glucose concentration in the plasma which in turn causes pathological metabolic reactions.

In the usual human nutrition, glucose-containing foodstuffs play an important role. The most important glucose sources in the human nutrition are glucose polymers from vegetable foodstuffs. The glucose molecules thereby are linearly linked in a so-called α 1→4-glycosidic bond (amylose). By so-called α 1→6-glycosidic branchings, amyloses become amylopectins. Each branch, however, consists in turn of glucoses in an α 1→4-glycosidic bond. The glucose polymer correspondingly branched from foodstuffs from animals is called glycogen. The α 1→4-glycosidic bond, as well as the α 1→6-glycosidic branching points can rapidly be split and catabolized by endogenous hydrolases, e.g. amylases, amyloglucosidases and maltases, into maltodextrines, maltose and finally into glucose.

With administration of the usual glucose-containing nutritions, the glucose is very rapidly taken up into the bloodstream, so that as early as 15 minutes later and hence postprandially, high glucose concentrations can be observed which, however, decrease again rapidly in humans having a sound metabolism. This rapid decrease of the glucose concentration in the plasma is conditioned by the rapid uptake of the glucose into the metabolism of the cells.

In the case of a diabetic, this inflow of the glucose into the cells is disturbed so that the depicted decrease, in dependence on the pathologic degree of the diabetes mellitus, takes place in a delayed manner, and hence, high glucose concentrations persist in the plasma.

Even diabetics, however, cannot renounce of glucose-containing foodstuffs since glucose represents a basic substance for the energy metabolism of all cells. Moreover, glucose-containing carbohydrates traditionally are important components of human nutrition. The renunciation of glucose-containing carbohydrates hence will also entail—apart from the metabolic significance of a lack of glucose—a considerable restriction of the quality of life for the diabetic.

It would now be desirable for the diabetic that the food intake would not lead to the described high fluctuations of the glucose concentration in the plasma. For achieving this, various concepts have already been developed. For one, one has tried to achieve a continuity of the blood glucose concentration in that the carbohydrate portion in nutrition is reduced in favor of the fat portion. For this purpose, the company Abbott offers, for example, the nutrition Glucerna®. The portion in percent of the nutritional energy in this known nutrition is as follows: 50.7% of the energy from fat, 16.9% of the energy from proteins, and 32.4% of the energy from carbohydrates.

It has also been already attempted to reduce the blood glucose fluctuations by administering nutritions containing as the carbohydrates a mixture of carbohydrates which are of a good absorption and of a poor absorption. Reference is made in this respect to the documents EP 0 768 043 and WO 96/31129, respectively.

It is the object of the present invention to provide a carbohydrate mixture and a nutrition containing same, by means of which the postprandial blood glucose concentration increase after eating can be moderated.

BRIEF DESCRIPTION OF THE DRAWING

FIG. 1: Comparison of glucose release for inventive carbohydrates from Examples 1a and 6 with that of two unmodified carbohydrates.

DETAILED DESCRIPTION OF THE INVENTION

The inventive carbohydrate mixture is characterized in that it contains at least one carbohydrate modified in the meaning according to the invention. The inventive carbohydrate mixture can thereby exclusively consist of one or several of such modified carbohydrate/s or of a mixture of usual unmodified carbohydrates used for nutritional purposes, and at least one carbohydrate modified according to the invention.

For the preparation of the carbohydrates modified according to the invention, likewise serve usual carbohydrates used for nutritional purposes. Two groups of carbohydrates are thereby used.

The first group concerned are carbohydrates having a digestible glucose-containing base structure. To this base structure, at least a further glucose residue or another carbohydrate residue is coupled and hence linked thereto. Said other coupled carbohydrate residue concerned can be a monosaccharide, disaccharide, oligosaccharide or a polysaccharide. Said other carbohydrate residue moreover can have further glucose units or can also be free from such glucose units. Such carbohydrates modified according to the invention having a digestible base body (or core), and a thereto coupled further glucose residue and/or carbohydrate residue, are designated as carbohydrates a) within the framework of the present documents.

Among the digestible glucose-containing base bodies count, for example, starch and the components thereof.

By adding or coupling a further glucose residue and/or another carbohydrate residue to these usual digestible glucose-containing base bodies, so-called "slow release carbohydrates" are obtained, the degradability or digestibility of which in the gastrointestinal tract is impeded in that the so-called residues are coupled.

The second group of carbohydrates which can be used and modified according to the invention, possesses a non-digestible carbohydrate as the base body, to which at least a glucose residue and/or a glucose-containing carbohydrate residue is coupled, and hence linked thereto. These modified carbohydrates are designated as carbohydrates b) within the framework of the present documents.

Such base bodies of non-digestible carbohydrates are, for example, dextranes and insulins and celluloses. These serve as carriers of the thereto linked or coupled glucose residues and/or glucose-containing carbohydrate residues or glucose oligomers. The thereto coupled carbohydrate residues concerned can thereby be the same as with the carbohydrates a). However, the coupled carbohydrate residues must contain at least one glucose unit. These coupled glucose-containing carbohydrate residues can only slowly be released again from the thereto linked carrier. The amount of the maximally releasable glucose thereby corresponds to that amount of glucose, which was previously coupled to the base body.

The carbohydrates a) and b) modified according to the invention can be degraded in an impeded manner (this applies to carbohydrates a)) by endogenous glycosidases (e.g. hydrolases in saliva, pancreatic juice, small intestine disaccharidases), or can be degraded at all, despite the indigestible base body, and hence represent "slow release carbohydrates".

The carbohydrates modified according to the invention thereby are preferably obtained by an enzymatic coupling of the therewith linked carbohydrate residues. The carbohydrates a) and b) modified according to the invention have a degree of polymerization (DP) of at least 2 (i.e. disaccharides) up to some 100,000. A range from DP 3 up to 100 is preferred.

The carbohydrates a) and b) modified according to the invention therewith consist—such as explained above—of a base body which is a priori digestible or of a base body which is not a priori digestible, whereby said base body is coupled with at least one further carbohydrate residue, in particular by enzymatic linkage. The base body, as well as the thereto coupled carbohydrate residue, in the simplest case each are comprised of at least one monosaccharide. The ratio between the number of monosaccharide units in the base body and the number of the monosaccharide units in the group/s linked with the base body, however, preferably is 1:10 up to 100:1.

When a base body is comprised of at least three monosaccharide units, then the linkage with a further monosaccharide either leads to an extension of the base body or to a branching of the base body. When the base body is comprised of more than three monosaccharides, then several branchings can be installed. Such branchings, in the meaning according to the invention, lead to an additional steric inhibition of endogenous glycosidases. By means of such branchings, "slow release carbohydrates" can be obtained in a targeted manner.

The digestible base body or carbohydrate of the modified carbohydrate a) concerned, preferably is starch, amylose, amylopectin and dextrines and the components thereof.

The non-digestible base body or carbohydrate of the modified carbohydrate b) concerned, preferably are fructans, β-glucans, cellulose, pectins, galacturonans, galactans, galactomannans, β-galactooligosaccharaides, α-galactooligosaccharides, fucoidans, mannans, xylans, xyloglucans, laminarin, chitins, chitosans, hyaluronic acids, chondroitins, proteoglycans, glucurono-oligosaccharides, arabinans, arabinoxylans, arabinogalactans, rhamnooligosaccharides, xanthans, alginates, agar, carragheenans, hemicelluloses, natural gum, enzymatically produced, carbohydrates (e.g. galactooligosaccharides and glucooligosaccharides), bacterial carbohydrates (e.g. xanthans, dextrans and sialyloligosaccharaides). N-glycoprotein-oligosaccharides, O-glycoprotein-oligosaccharides and glycolipid-oligosaccharides.

The inventive carbohydrate mixture in the simplest case can therewith be comprised of one or several carbohydrate/s a) modified according to the invention.

The inventive carbohydrate mixture moreover can be comprised of one or more carbohydrate/s b) modified according to the invention.

The inventive carbohydrate mixture can moreover be comprised of a mixture of one or several carbohydrate/s a) modified according to the invention and one or several carbohydrate/s b) modified according to the invention.

Moreover, in the inventive carbohydrate mixture, apart from one or several carbohydrate/s a) modified according to the invention and/or apart from one or several carbohydrate/s b) modified according to the invention, usual unmodified carbohydrates c) used for the preparation of nutrition can be present which accordingly have not been modified in the inventive sense. Assessing whether in a carbohydrate mixture the therein present carbohydrate has to be regarded as a carbohydrate a), a carbohydrate b) or a carbohydrate c), it has to be taken into account that among the carbohydrates c) count not only those which have been added a priori unmodified during the preparation of the carbohydrate mixture or a nutrition provided therewith. On the contrary, among the carbohydrates c) count also those carbohydrates which have not reacted during the preparation process of carbohydrates modified according to the invention, and which accordingly have not been modified and hence have not been changed, either. In other words, this means the following. When in an inventive modification some of the base bodies used are not coupled with a further carbohydrate residue and hence remain unmodified, then they have to be counted among the carbohydrates c). The same applies to the carbohydrate residues intended to be coupled with the base body, be it digestible or indigestible. Also those carbohydrate residues which have not reacted and hence have not been coupled to a base body, count among the carbohydrates c).

Thereby, it is of importance that the used mixture of carbohydrates is composed in such a manner that in an in-vitro digestion system based on pancreatine, at least 10% by weight less glucose is released per time unit as compared with a carbohydrate mixture containing the same amount by weight of non-modified carbohydrate or of non-modified carbohydrates and/or of the starter carbohydrates used for the preparation of the modified carbohydrate/s a) and b). In other words, this means the following. The release of glucose from the inventive carbohydrate mixture is reduced by at least 10% as compared to the release of glucose from a carbohydrate mixture containing the same amount by weight of carbohydrates, whereby these carbohydrates are composed of the sum of non-modified carbohydrates, insofar as these are present, and the starter carbohydrates used for the preparation of the modified carbohydrates a) and b). This 10% reduction relates to a period from the start of the digestion up to 90 minutes after the start of the digestion.

For explaining the latter, it is assumed that an inventive carbohydrate exclusively is comprised of a carbohydrate a) modified according to the invention. For the preparation of this inventive carbohydrate a), 5 g of a glucose residue or of another carbohydrate residue are linked with 15 g of a carbohydrate having a digestible glucose-containing base body. With this, 20 g of carbohydrate a) modified according to the invention are obtained.

The digestibility of this carbohydrate a) modified according to the invention now has to be changed so that in an in-vitro digestion system on the basis of pancreatine, at least 10% by weight less glucose is released per time unit as compared with the initial carbohydrate mixture and hence with the carbohydrate mixture used prior to the coupling consisting of 15 g base body and 5 g of the glucose residue and/or carbohydrate residue to be coupled therewith.

The analogue applies in case the inventive carbohydrate mixture is comprised of one or several carbohydrate/s b) modified according to the invention or of a mixture of one or several carbohydrate/s a) modified according to the invention and one or several carbohydrate/s b). The analogue applies moreover when, apart from the carbohydrate/s a) modified according to the invention and/or the carbohydrate/s b) modified according to the invention, one or several usual non-modified carbohydrate/s is/are present, as well.

Thereby, it has to be considered—as explained above—that with a coupling of the glucose residues or of the other carbohydrate residues with the described base body, a glucose residue or another carbohydrate residue is not forcibly coupled to each base body molecule. Neither must each initially used glucose residue or another carbohydrate residue forcibly enter into a coupling reaction with a base body rather it can still be present in the original form even after the realization of the coupling reaction. These non-converted residues then have to be counted among the carbohydrates c).

It is only decisive that in an in-vitro digestion system on the basis of pancreatine, at least 10% by weight less glucose is released per time unit as compared with a mixture of the initially used starter carbohydrates.

The digestibility of carbohydrates mentioned here incidentally is determined by way of in-vitro experiments in that the inventive carbohydrate mixtures are incubated by means of pancreatine of pig origin (e.g. Sigma). The concentration used of pancreatine in water thereby is 10 g/l with 1 mM serin protease inhibitor Pefabloc (Boehringer Mannheim) and 0.02% $NaN_3$. 1 ml of pancreatine solution sterilized by filtration are admixed with 200 µl of the carbohydrate mixture solution (10 mg/ml) and 800 µl of water, and are incubated at 37° C. for 90 minutes. The released glucose is determined by means of an enzymatic test (e.g. Boehringer Testkit, Order-No. 139106). At the points of time 5 min, 10 min, 15 min, 20 min, 30 min, 45 min, 60 min, 75 min and 90 min, aliquots are taken for this purpose. The reaction is stopped by incubation at 95° C. for 5 min. Lactose is used as the negative control for the pancreatine digestion. Maltodextrin serves as the positive control. An example of such a digestion for two inventive slow release carbohydrate mixtures is shown in the illustration. In this illustration, the glucose release for two inventive carbohydrate mixtures, namely those described in the Examples 1a and 6, are compared with the glucose release from a carbohydrate mixture consisting of the starter carbohydrates of Example 1a, namely saccharose and maltodextrin. The difference between the curves for Example 1a and for the unmodified Example 1a hence is that the carbohydrates used in Example 1a have been treated with dextransucrase, whereas such a treatment has not been carried out in the unmodified Example 1a.

The glucose released delayed from the inventive carbohydrate mixture after eating immediately leads to lower peak glucose concentrations and even beyond the immediate postprandial phase to relative constant glucose concentrations in the plasma, whereby the glucose can be metabolized by diabetics in spite of the existing lack of insulin, and is thus available as an important energy carrier. The reduced digestibility moreover causes a part of the inventive carbohydrate mixture to reach the large intestine, where a further utilization of the inventive carbohydrate mixture ensues by the existing intestinal flora. Apart from further making available glucose for the organism, this has the positive effect of stimulating the intestinal micro-flora, whereby digestion problems can be reduced.

The used carbohydrate structures modified according to the invention thereby are comprised of a base body or core, and of therewith linked terminal groups. The cores are influenced with respect to their digestibility by the terminal groups, thereby causing in the end a change of the cinetics of the intraluminal digestion. This changed digestibility has an effect on the cinetics of the glucose uptake from the intestine into the blood stream, so that the glucose peak usually arising in the plasma after 15 minutes (Petrides et al; from "Diabetes mellitus", $5^{th}$ ed. (Ed. Petrides, Weiss, Loeffler, Wieland) 1985, Urban & Schwarzenberg, Munich) is avoided with the administration of an inventive carbohydrate mixture or of a nutrition containing said carbohydrate mixture.

Thus, the subject matter of the invention is also a nutrition for diabetics or a foodstuff for diabetics containing the inventive carbohydrate mixture. The inventive carbohydrate mixture thereby constitutes the carbohydrate component of said foodstuff. Apart from that, other components can be present, such as fats and proteins, as well as, if required, further usually used ingredients. The inventive carbohydrate mixture can moreover be used as a tube food or can be used for preparing tube foods.

A further field of application relates to the pharmaceutical sector. Thus, the inventive carbohydrate mixture can also be used in pharmaceuticals.

For the preparation of the carbohydrates a) and b) modified according to the invention by means of enzymatic linkage, the following enzyme classes are preferably used:

A. Natural and/or recombinant glycosidases from biological sources such as plants, animals and micro-organisms functioning via a reverse hydrolase or in a transglycosilation reaction towards the synthesis. The β-galactosidase (EC 3.2.1.23) from *Aspergillus oryzae* can, for example, be used. As the further sources for the β-galactosidase serve primarily micro-organisms or monocellular organisms such as, for example, *Kluiveromyces lactis, Streptococcus thermophilus, Lactobacillus bulgaficus* and *Bacillus circulans*.

Moreover, α-glucosidases, e.g. amyloglucosidase from *Aspergillus niger* (EC 3.2.1.3), α-amylase, e.g. from *Bacillus amyloliquefaciens* (EC 3.2.1.1) and e.g. from *Alcaligenes* spec., pullulanases (EC 3.2.1.41) and/or β-glucosidases, e.g. those from sweet almonds (EC 3.2.1.21) or cellulase, e.g. from *Trichoderma viride* (EC 3.2.1.4) can be used. Also N-acetyl-β-D-glucosamidase, e.g. from bovine kidneys, can be used.

B. Natural and/or recombinant transferases from biological sources such as plants, animals and micro-organisms, which do not require activated monosaccharides/oligosaccharides as a substrate. Thereto count cyclomaltodextrine glucanotransferase CGT (EC 2.3.1.19), e.g. from *Bacillus rnacerans*, and dextransucrase (EC 2.4.1.5), e.g. from *Leuconostoc mesenteroides*. Among them count further transglucosidase, e.g. from *Aspergillus niger* (EC 2.4.1.24).

And/or

C. Natural and/or recombinant transferases from biological sources such as plants, animals and micro-organisms, which require activated monosaccharides as the substrate, such as, for example, galactosyl transferase e.g. from bovine milk (EC 2.4.1.22). This enzyme transfers galactose from UDP galactose as the donor in β1→4 bonds to glucose residues.

The following examples serve the purpose of explaining the invention.

EXAMPLE 1

Preparation of a carbohydrate a) modified according to the invention, consisting of a digestible base body and at least one glucose residue linked therewith.

Variant A)

20 g of saccharose and 100 g of maltodextrine (low-molecular amylose having a good water-solubility and a varying chain length) in 500 ml of 20 mM acetate buffer are incubated at pH 5.2 with 2,000 U dextrane sucrase from *Leuconostoc mesenteroides* (EC 2.4.1.24) for 5 h at 37° C. Thereby, at feast one glucose residue originating from the saccharose is transferred to the maltodextrine units. The thus obtained maltodextrine is purified after heat denaturation of the enzyme (5 min at 100° C.) by ultra-filtration. 40 g of maltodextrines modified by at least one glucose residue are obtained.

Variant B)

5 g of maltose and 15 g of maltodextrine (low-molecular amylose having a good water-solubility and a varying chain length) in 500 ml of 10 mM acetate buffer are incubated at pH 4.0 with 10,000 U transglucosidase from *Aspergillus niger* (EC 2.4.1.24) for 5 h at 37° C. Thereby, at least one glucose residue originating from the maltose is transferred to the maltodextrine units. The thus obtained maltodextrine is purified after heat denaturation of the enzyme (5 min at 100° C.) by ultra-filtration. 12.5 g of maltodextrines modified by at least one glucose residue are obtained.

Variant C)
The same procedure as with variant A) is applied, whereby, however, the incubation takes place at 50° C. instead of 37° C. 40 g of maltodextrines modified by at least one glucose residue are obtained.

Variant D)
The same procedure as with variant B) is applied, whereby, however, the incubation takes place at 50° C. instead of 37° C. 12.5 g of maltodextrines modified by at least one glucose residue are obtained.

Variant E)
The same procedure as with variant A) is applied, whereby, however, the incubation takes place at 10° C. instead of 37° C. 40 g of maltodextrines modified by at least one glucose residue are obtained.

Variant F)
The same procedure as with variant B) is applied, whereby, however, the incubation takes place at 10° C. instead of 37° C. 12.5 g of maltodextrines modified by at least one glucose residue are obtained.

EXAMPLE 2

Preparation of a carbohydrate a) modified according to the invention from a digestible base body and at least one glucosecontaining carbohydrate residue coupled thereto.

Onto 30 g of maltodextrines, glucan residues from 10 g of amylase or amylopectin (from starch) are transferred by means of cyclomaltodextrine glucanotransferase CGT (EC 2.4.1.19) from *Bacillus macerans* CGT.

EXAMPLE 3

Preparation of a carbohydrate a) modified according to the invention from a digestible base body and at least one carbohydrate residue coupled thereto not containing glucose.

Transfer of galactose to maltodextrine.

Variant A)
100 g of maltodextrine (low-molecular amylose having a good water-solubility and a varying chain length) and 10 g of lactose are incubated in 500 ml of 40 mM NaOAc buffer at 5.0 pH with 2,000 U β-galactosidase from *Kluiveromyces lactis* for 5 h at 30° C. The thus obtained galactosilyzed maltodextrines are purified after heat denaturation of the enzyme (5 min at 100° C.) by ultra-filtration.

Variant B)
The same procedure is applied as with variant A), whereby, however, it is incubated at 50° C. instead of 37° C.

Variant C)
The same procedure is applied as with variant A), whereby, however, it is incubated at 10° C. instead of 37° C.

EXAMPLE 4

Preparation of a carbohydrate b) modified according to the invention from a indigestible base body and at least one glucose residue coupled thereto.

Variant A)
50 g of cello-oligosaccharides (DP2 to DP10) and 15 g of maltose in 500 ml 20 mM acetate buffer are incubated at pH 5.2 with 30,000 cyclomaltodextrine glucanotransferase CGT (EC 2.4.1.19) from *Bacillus macerans* CGT for 5 h at 37° C. The thus obtained modified cello-oligosaccharides are purified after heat denaturation of the enzyme (5 min at 100° C.) by ultra-filtration.

Variant B)
The same procedure is applied as with variant A), whereby, however, it is incubated at 50° C. instead of 37° C.

Variant C)
The same procedure is applied as with variant A), whereby, however, it is incubated at 10° C. instead of 37° C.

EXAMPLE 5

Preparation of a carbohydrate b) modified according to the invention from a indigestible base body and at least one glucose-containing carbohydrate residue coupled thereto.

Variant A)
50 g of cellooligosaccharides (DP2 to DP10) and 15 g of maltodextrine in 500 ml 20 mM acetate buffer are incubated at pH 5.2 with 30,000 U cyclomaltodextrine glucanotransferase CGT (EC 2.4.1.19) from *Bacillus macerans* CGT for 5 h at 37° C. The thus obtained modified cello-oligosaccharides are purified after heat denaturation of the enzyme (5 min at 100° C.) by ultra-filtration.

Variant B)
The same procedure is applied as with variant A), whereby, however, it is incubated at 50° C. instead of 37° C.

Variant C)
The same procedure is applied as with variant A), whereby, however, it is incubated at 10° C. instead of 37° C.

EXAMPLE 6

Preparation of a carbohydrate b) modified according to the invention from a indigestible base body and at least one glucose-containing carbohydrate residue coupled thereto.

Variant A)
180 g of cellobiose (DP2) and 80 g maltodextrine in 500 ml of 20 mM acetate buffer are incubated at pH 5.2 with 100,000 U cyclomaltodextrine glucanotransferase CGT (EC 2.4.1.19) from *Bacillus macerans* CGT for 5 h at 37° C. The thus obtained modified cellobiose (about 85 g) is purified after heat denaturation of the enzyme (5 min at 100° C.) by ultra-filtration.

Variant B)
The same procedure is applied as with variant A), whereby, however, it is incubated at 50° C. instead of 37° C.

Variant C)
The same procedure is applied as with variant A), whereby, however, it is incubated at 10° C. instead of 37° C.

The following diagram shows the digestion or the digestive process of the carbohydrate mixtures of the Examples 1A and 6.

The release of glucose from these inventive carbohydrate mixtures—determined in an in-vitro digestion system on the basis of pancreatine—is reduced by at least 10% per time unit as compared with a carbohydrate mixture containing the same amount per weight of non-modified carbohydrates. The glucose, for example, is determined by the enzymatic method, for instance by means of the Boehringer Testkit (Order No. 139106).

The invention claimed is:

1. A method of treating a diabetic to control blood glucose levels which comprises administering to the diabetic an effective amount of a modified carbohydrate obtained by coupling or linking, respectively, a usual carbohydrate used for nutritional purposes with a further carbohydrate residue, or of a mixture of several of such modified carbohydrates, whereby the modified carbohydrate comprises a base body from a digestible glucose-containing carbohydrate in the form of a digestible glucan which is a maltodextrin, at least one glucose residue and/or another carbohydrate residue having been coupled and hence linked with said base body, and whereby the modified carbohydrates are maltodextrins i) which were derivatized in a transglycosilation reaction by means of a transglucosidase under formation of glycosidic bonds with glucose in the α 1→2 position or α 1→3 position, ii) which were derivatized by means of β-galactosidase under formation of glycosidic bonds with galactose in the β 1→3 position, β 1→4 position or the 1→6 position, and/or iii) to the free hydroxyl groups of which at the C2 or C3 carbon atom, glucan residues from amylose or amylopectin (from starch) were transferred by means of cyclomaltodextrin glucanotransferase CGT (EC 2.4.1.19) from *Bacillus macerans* CGT; and wherein the modified maltodextrin releases at least 10% less glucose in an in vitro digestion system than the unmodified one.

2. The method according to claim 1, wherein that, as transglucosidase, dextransucrase from *Leuconostoc mesenteroides* (EC 2.4.1.24) and saccharose are used as the source, for the glucose to be coupled.

3. The method according to claim 1, wherein lactose (Gal β 1→4 Glc) and/or melibiose (Gal α 1→6 Glc) are used, as the source for the galactose to be coupled.

4. The method according to claim 2, wherein, as transglucosidase, dextransucrase from *Leuconostoc mesenteroides* (EC 2.4.1.24) and saccharose are used as the source, in excess, for the glucose to be coupled.

5. The method according to claim 3, wherein lactose (Gal β 1→4 Glc) and/or melibiose (Gal α 1→6 Glc) are used, in excess, as the source for the galactose to be coupled.

6. A method of treating a diabetic to control blood glucose levels which comprises administering to the diabetic an effective amount of a modified carbohydrate obtained by coupling or linking, respectively, a usual carbohydrate used for nutritional purposes with a further carbohydrate residue, or of a mixture of several of such modified carbohydrates, whereby the modified carbohydrate comprises a base body from a digestible glucose-containing carbohydrate in the form of a digestible glucan which is a maltodextrin, at least one glucose residue and/or another carbohydrate residue having been coupled and hence linked with said base body, and whereby the modified carbohydrates are maltodextrins i) which were derivatized in a transglycosilation reaction by means of a transglucosidase under formation of glycosidic bonds with glucose in the α 1→2 position, and α 1→3 position, ii) which were derivatized by means of β-galactosidase under formation of glycosidic bonds with galactose in the β 1→3 position, β 1→4 position or the 1→6 position, and/or iii) to the free hydroxyl groups of which at the C2 or C3 carbon atom, glucan residues from amylose or amylopectin (from starch) were transferred by means of cyclomaltodextrin glucanotransferase CGT (EC 2.4.1.19) from *Bacillus macerans* CGT; and wherein the modified maltodextrin releases at least 10% less glucose in an in vitro digestion system than the unmodified one.

* * * * *